US008511889B2

(12) United States Patent
Choikhet et al.

(10) Patent No.: US 8,511,889 B2
(45) Date of Patent: Aug. 20, 2013

(54) FLOW DISTRIBUTION MIXER

(75) Inventors: Konstantin Choikhet, Boeblingen (DE); Klaus Witt, Boeblingen (DE); Martin Baeuerle, Boeblingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 736 days.

(21) Appl. No.: 12/702,147

(22) Filed: Feb. 8, 2010

(65) Prior Publication Data

US 2011/0192217 A1 Aug. 11, 2011

(51) Int. Cl.
*B01F 5/06* (2006.01)

(52) U.S. Cl.
USPC ............ 366/336; 138/40

(58) Field of Classification Search
USPC ................ 366/144–149, 173.1, 173.2, 174.1, 366/336–341, 349, 181.5, DIG. 1, DIG. 2, 366/DIG. 3, DIG. 4; 165/109.1; 138/37, 138/40, 42; 137/325.8, 599
See application file for complete search history.

(56) References Cited

U.S. PATENT DOCUMENTS 1,409,259 A * 3/1922 Sykora .......................... 239/565
2,734,224 A * 2/1956 Winstead ...................... 425/190
3,381,336 A * 5/1968 Wells ......................... 425/378.2
3,394,924 A * 7/1968 Harder .......................... 366/338
3,459,407 A * 8/1969 Hollis et al. .................. 366/338
3,476,521 A * 11/1969 Wise ............................ 422/138
3,533,594 A * 10/1970 Segmuller ..................... 249/107
3,924,989 A * 12/1975 Althausen et al. ............ 425/130
4,017,240 A * 4/1977 Nelson ...................... 425/192 R
4,027,857 A * 6/1977 Cunningham ................ 366/340
4,279,862 A * 7/1981 Bretaudiere et al. ............ 422/72
4,354,932 A * 10/1982 McNeil ...................... 210/198.2
4,537,217 A * 8/1985 Allen, Jr. .................. 137/561 A
4,550,681 A * 11/1985 Zimmer et al. ............... 118/410
4,999,102 A * 3/1991 Cox et al. ...................... 210/137
5,289,224 A * 2/1994 Devaney et al. .............. 396/626
5,296,375 A * 3/1994 Kricka et al. ..................... 435/2
5,304,487 A * 4/1994 Wilding et al. ................. 435/29
5,354,460 A * 10/1994 Kearney et al. ............ 210/198.2
5,427,946 A * 6/1995 Kricka et al. .............. 435/288.5
5,486,335 A * 1/1996 Wilding et al. ............... 422/400
5,540,849 A * 7/1996 Dugan ......................... 210/767
5,587,128 A * 12/1996 Wilding et al. ................. 422/50
5,635,358 A * 6/1997 Wilding et al. ................ 435/7.2
5,637,469 A * 6/1997 Wilding et al. .............. 435/7.21
5,783,129 A * 7/1998 Shirai et al. ................... 264/136

(Continued)

FOREIGN PATENT DOCUMENTS

EP 309596 4/1989
WO WO 8803052 A1 * 5/1988

*Primary Examiner* — Charles E Cooley

(57) ABSTRACT

A mixer for mixing a fluid having a property varying along a flow direction of the fluid includes an inlet configured for receiving an inlet flow, an outlet configured for providing an outlet flow, and a plurality of flow channels coupled between the inlet and the outlet. The mixer also includes a flow distributor for distributing the inlet flow into the plurality of flow channels so that each flow channel receives a partial flow from the inlet flow, and a flow combiner for combining the partial flows from the plurality of flow channels to the outlet flow. Each flow channel has a first flow section having a hydraulic resistance substantially representing a hydraulic resistance of the flow channel. One or more of the flow channels each have a second flow section coupled in series with the first flow section of the respective flow channel.

15 Claims, 3 Drawing Sheets

200 230 260L 260 270 270L 220 230A 260A 230B 260B 230C 260C 260D 240 270B 270C 270D 210 250

(56) References Cited

U.S. PATENT DOCUMENTS

| | | | | |
|---|---|---|---|---|
| 5,866,345 | A * | 2/1999 | Wilding et al. | 435/7.21 |
| 5,938,333 | A * | 8/1999 | Kearney | 366/336 |
| 5,955,029 | A * | 9/1999 | Wilding et al. | 422/68.1 |
| 5,992,453 | A * | 11/1999 | Zimmer | 137/561 A |
| 6,156,273 | A * | 12/2000 | Regnier et al. | 422/70 |
| 6,170,981 | B1 * | 1/2001 | Regnier et al. | 366/336 |
| 6,296,020 | B1 * | 10/2001 | McNeely et al. | 137/806 |
| 6,333,019 | B1 * | 12/2001 | Coppens | 423/659 |
| 6,540,896 | B1 * | 4/2003 | Manz et al. | 506/39 |
| 6,601,613 | B2 * | 8/2003 | McNeely et al. | 137/833 |
| 6,616,327 | B1 * | 9/2003 | Kearney et al. | 366/340 |
| 6,629,775 | B2 * | 10/2003 | Choikhet et al. | 366/336 |
| 6,637,463 | B1 * | 10/2003 | Lei et al. | 137/803 |
| 6,709,559 | B2 * | 3/2004 | Sundberg et al. | 204/604 |
| 6,742,924 | B2 * | 6/2004 | Kearney | 366/336 |
| 6,749,413 | B2 * | 6/2004 | Fare' | 425/72.2 |
| 7,014,442 | B2 * | 3/2006 | Haynes et al. | 425/131.5 |
| 7,021,608 | B2 * | 4/2006 | Lavemann et al. | 261/23.1 |
| 7,040,555 | B2 * | 5/2006 | Miinalainen et al. | 239/562 |
| 7,066,641 | B2 * | 6/2006 | Honda | 366/340 |
| 7,390,408 | B2 * | 6/2008 | Kearney et al. | 210/282 |
| 7,494,770 | B2 * | 2/2009 | Wilding et al. | 435/6.11 |
| 7,575,635 | B2 * | 8/2009 | Perttila et al. | 118/411 |
| 7,829,027 | B2 * | 11/2010 | Osterloh et al. | 422/401 |
| 7,939,033 | B2 * | 5/2011 | Lavric et al. | 422/503 |
| RE42,882 | E * | 11/2011 | Kearney | 366/336 |
| 8,231,265 | B2 * | 7/2012 | Ozawa et al. | 366/336 |
| 2002/0021620 | A1 * | 2/2002 | Choikhet et al. | 366/337 |
| 2002/0196706 | A1 * | 12/2002 | Kearney | 366/336 |
| 2003/0039169 | A1 * | 2/2003 | Ehrfeld et al. | 366/336 |
| 2004/0037161 | A1 * | 2/2004 | Honda et al. | 366/176.1 |
| 2004/0145967 | A1 * | 7/2004 | Honda | 366/336 |
| 2004/0213084 | A1 * | 10/2004 | Kearney | 366/336 |
| 2005/0000879 | A1 * | 1/2005 | Kearney et al. | 210/287 |
| 2005/0092681 | A1 * | 5/2005 | Higashino et al. | 210/634 |
| 2006/0280029 | A1 * | 12/2006 | Garstecki et al. | 366/336 |
| 2007/0077169 | A1 * | 4/2007 | Yang et al. | 422/57 |
| 2010/0226202 | A1 * | 9/2010 | Vassilicos et al. | 366/336 |
| 2011/0080802 | A1 * | 4/2011 | Vassilicos et al. | 366/337 |
| 2011/0176965 | A1 * | 7/2011 | Castro et al. | 422/69 |

* cited by examiner

FLOW DISTRIBUTION MIXER

BACKGROUND

The present invention relates to a flow distribution mixer distributing the inlet flow into a plurality of flow channels and then combining the partial flows from the plurality of flow channels to the outlet flow, in particular for high performance liquid chromatography application.

In high performance liquid chromatography (HPLC), a liquid has to be provided usually at a very well controlled flow rate (e.g. in the range of microliters to milliliters per minute), at a very well controlled composition (e.g. in the range of 0.3% or better) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid containing compounds to be separated is driven through a stationary phase (e.g. contained in a chromatographic column), thus separating different compounds of the sample which may then be identified.

The mobile phase, for example, a solvent, is pumped under high pressure typically through a column filled with packing material, and the sample (e.g. a chemical or biological mixture) to be analyzed is injected into the stream of the mobile phase and with that is transported to the column. As the sample passes through the column driven by the liquid flow, the different compounds, each one having a different affinity for the packing medium, move through the column with different velocities. Those compounds having higher affinity to the stationary phase (e.g. a packing medium) move more slowly through the column than those having lower affinity, and this velocity differences results in the compounds being separated from one another as they pass through the column.

During operation, a flow of the mobile phase, typically driven by a high pressure chromatographic pump, traverses the column filled with the stationary phase, and due to the interactions between the mobile, the stationary phase and sample components a separation of different compounds may be achieved. As a result of flow passing through the stationary phase and depending on the physical properties of the stationary phase and the mobile phase, a relatively high pressure drop takes place along the column. The composition of the mobile phase is in many cases controlled by the pump operation, as the pump blends single flows of mobile phase constituents according to the pump settings or program. These flows are then combined together to provide a mixed flow of the mobile phase or eluent. The composition and the flow rate of the mobile phase are usually precisely controlled.

The fluctuations of the mixing ratio in an eluent flow generated e.g. by an HPLC pump can lead to undesired base line noise, bad reproducibility of the analysis or to separation performance deterioration. For certain applications, e.g. separations using eluents with UV-absorbing additives, the strict requirements to the constancy or smoothness of the eluent composition over the separation time cannot be satisfied without using additional mixing appliances which disperse the zones with fluctuations of the eluent composition.

U.S. Pat. No. 6,629,775 B2, by the same applicant, discloses a mixing apparatus wherein a fluid is progressing from an inlet tubing to an outlet tubing. Every segment of the liquid is part by part transferred to the outlet channel via numerous restrictor channels. The distances between the restrictor channels determine a dispersion pattern for any segment of the flow, progressing from the inlet chamber in the form of a reservoir channel to the outlet. The nearer the outlet channels are placed one to another, the higher is the permeability to the outlet collector at the respective location. Delaying partial flows of the fluid with different flow delays and providing different flow volumes for the partial flows results in a predetermined flow distribution function thus determining a dispersion pattern. This allows for a continuous dispersion of a fluid property which is intended to be mixed, for instance to be homogenized, in accordance with a predefined fluid distribution function.

SUMMARY

It is an object of the invention to provide an improved flow distribution mixer, in particular for HPLC applications. The object is solved by the independent claim(s). Further embodiments are shown by the dependent claim(s).

According to embodiments of the present invention, a mixer is provided for mixing a fluid (which may be a liquid and/or a gas) having a property varying along a flow direction of the fluid. The mixer comprises an inlet configured for receiving an inlet flow, an outlet configured for providing an outlet flow, and a plurality of flow channels coupled between the inlet and the outlet. A flow distributor is provided for distributing the inlet flow into the plurality of flow channels, so that each flow channel receives a partial flow from the inlet flow. A flow combiner is provided for combining the partial flows from the plurality of flow channels to the outlet flow. Each flow channel comprises a first flow section having a hydraulic resistance substantially constituting entire hydraulic resistance of the flow channel for a partial flow. One or more of the flow channels each comprises a second flow section coupled in series with the first flow section of the respective flow channel. Each second flow section has a volume delaying a propagation of the fluid from the first flow section to the flow combiner by a time required by the respective partial flow to pass the volume of the respective second flow section. The distribution of the partial flows into the flow channels is substantially independent of the viscosity of the fluid.

As the distribution of the partial flows in such embodiments is substantially independent of the viscosity of the fluid, the mixer shows an improved characteristic in particular in such applications wherein the viscosity of the fluid varies over time. In HPLC, a typical application with varying viscosity is the so-called gradient mode, wherein the composition of the fluid is varied over time by changing the mixing ratio for a plurality of different solvents over time. As an example, two solvents water and acetonitrile (ACN; formula: $CH_3CN$) might be mixed for providing the mobile phase. During gradient mode, the mixing ratio between water and acetonitrile is varied (e.g. continuously or stepwise) over time, e.g. starting from hundred percent water to hundred percent acetonitrile. Viscosity of the mixed fluid (here the mobile phase) depends on the actual mixing ratio and thus becomes a function over time during gradient mode.

With the independency of the distribution of the partial flows onto the viscosity of the fluid, the mixing of the fluid as provided by the mixer also becomes substantially independent on the viscosity of the fluid, so that the mixer becomes in particular suitable and advantageous for applications wherein the viscosity of the fluid varies over time, such as in the aforementioned gradient mode in HPLC. Also, composition change of the eluent with this mixer embodiment takes place in a predictable and reproducible manner nearly independently on the special properties of the solvents.

In one embodiment, the hydraulic resistance of each of the plurality of flow channels is substantially equal. Accordingly, the partial flows become equal for all channels thus providing a homogeneous distribution of the partial flows into the flow channels.

In one embodiment, the volume of the second flow section is significantly larger than a volume of the first flow section of the respective flow channel. Accordingly, the hydraulic resistance of the channel is dominated by the first flow section.

In one embodiment, the flow distributor distributes the fluid into the first flow sections. Preferably, the flow distributor distributes the fluid substantially simultaneously into the first flow section.

In one embodiment, the mixer is configured so that a variation of the property of the fluid arrives substantially simultaneously at the first flow sections. This can be achieved, for example, by arranging the first flow sections to be coupled directly to the flow distributor, so that the flow distributor simultaneously distributes the fluid into the first flow sections of the flow channels.

In one embodiment, the mixer is configured in a way that the flow-through times of the partial flows through the first flow sections are substantially equal, so that all partial flows arrive substantially at the same time at the respective second flow sections or, if a respective flow channel does not have a second flow section, at the flow distributor.

In one embodiment, the flow-through times of the partial flows through the first flow sections are substantially neglectable to a characteristic duration of a variation of the varying property of the fluid. In other words, the property of the fluid is varying slower than each partial flow requires to flow through the first flow section.

In one embodiment, the mixer is configured so that the flow-through times of the partial flows through the first flow sections are substantially equal and neglectable to a characteristic duration of a variation of the varying property of the fluid. In such embodiment, the partial flows reach the second flow sections or, in case the respective flow channel does not comprise a second flow section, the flowed combiner substantially at the same time and much faster than the property of the fluid varies. Accordingly, it can be assumed that the mixing characteristic of the mixer is dominated by the distribution of characteristics of the second flow channels.

In one embodiment, a plurality of the second flow sections each has a different volume for delaying the partial flow of the respective flow channel by a different period. Accordingly, the resulting flow at the flow combiner will show a certain distribution function as defined by the respective delay volumes of the partial flows.

In one embodiment, the volume of each of a plurality of the second flow sections is configured so that the output flow has a desired flow delay profile with respect to the input flow.

In one embodiment, the volume of each second flow section is significantly larger than a volume of the first flow section of the respective flow channel. Thus, the timing behavior and in particular a delay of the partial flow is dominated by the volume of the respective second flow section.

In one embodiment, one or more of the second flow sections each comprises a chamber having a volume being significantly larger than a volume of the first flow section of the respective flow channel.

In another embodiment, one or more of the second flow sections each comprises a plurality of chambers arranged sequentially, in parallel or in a mixed connection pattern in the flow direction of the fluid. In one embodiment, successive chambers are coupled by a respective connecting section. Each chamber might have an (average or characteristic) cross section being significantly larger than an (average or characteristic) cross section of a respective connecting section coupled to such chamber. Alternatively or in addition, each chamber might have a chamber volume being significantly larger than a volume of a respective connecting section coupled to such chamber. Alternatively or in addition, a plurality of the connection sections can be arranged with respect to the respective chambers to force the fluid to flow in a direction sequentially varying respective to the direction of gravitational force. In latter embodiments, the forcing of the flow in or against a direction of a gravitational force can allow to provide embodiments, function of which is substantially independent on the position of the mixer, so that the mixing characteristics becomes substantially the same irrespective of an actual position of the mixer with respect to the direction of gravitational force. In such embodiments, it can be achieved that the mixing performance of the mixer is substantially the same even if the mixer is (arbitrarily) tilted/inclined with respect to a desired assembly direction for such mixer.

In one embodiment one or more of the second flow sections each comprises at least one direction change element configured for changing the flow direction of the fluid. Preferably, the direction change element comprises at least one first subsection having a first direction of flow of the fluid, and at least one second subject section having a second direction of flow of the fluid. The first direction of flow is inclined with respect to the second flow section of flow. The first direction of flow can be, for example, vertical, while the second direction of flow is horizontal. Alternatively or in addition, at least one of the first and second directions of flow has a direction component in the direction of gravitational force. In other words, at least one of the first and second directions is either in the direction of the gravitational force or being inclined thereto by an angle less than ninety degrees (so that the effect of gravity becomes noticeable). With such embodiments, the mixer can be provided to have mixing properties being substantially independent on the orientation of the mixer and the aforementioned (with respect to orientation-independency) applies accordingly.

In one embodiment, each flow channel comprises a respective first flow section and a respective second flow section coupled in series. The hydraulic resistance of the first flow section is significantly larger than a hydraulic resistance of the second flow section, so that the hydraulic resistance of the flow channel is dominated by the first flow section.

In one embodiment the hydraulic resistance of the first flow section is in the range of 2-100000 times larger than the hydraulic resistance of the second flow section. Preferably, the hydraulic resistance of the first flow section is about 5-500 times larger than the hydraulic resistance of the second flow section, and more preferably about ten to hundred times.

In one embodiment, in each flow channel a first cross section of the first flow section is significantly smaller than a second cross section of the second flow section, so that the hydraulic resistance of the flow channel is dominated by the first cross section of the first flow section.

In one embodiment, each first flow section is substantially equal in length in flow direction of the fluid. In other words, all first flow sections are substantially equally long.

The fluid can be a liquid, a gas, a supercritical fluid, or mixture.

The varying property of the fluid can be a physical and/or chemical property varying along the flow direction of the fluid.

The varying property of the fluid can be temperature, composition, and viscosity and/or elution strength varying along the flow direction of the fluid. In case the fluid is comprised of plural fluid components, e.g. different solvents such as water, acetonitrile, methanol, or isopropanol, or it contains dissolved additives such as buffers, salts, ion-pairing modifiers or other additives, e.g. TFA (trifluoroacetic acid, the composition of the fluid describes the amount or ratio of each individual fluid component present at a certain position or time along a flow path of the fluid. Variations in composition can occur e.g. in case a pump for pumping the fluid receives only one fluid component at a time (wherein the pump sucks fluid into its pumping chamber) and takes in the mixture components sequentially in the course of a pumping cycle. Such "package-wise" supply of fluid with the individual packages, each having a different fluid composition content, is commonplace in HPLC applications, in particular during gradient mode, as disclosed e.g. in EP 309596 B1. Embodiments of the present invention allow mixing such packages to provide a substantially homogeneous mixture of the fluid components. Another source of composition variations can be transients in the reciprocating operation of channels in a multi-channel pump, during which the flows of the individual mixture components predestinated for mixing are disturbed.

In one embodiment, a mixer is provided for mixing a fluid having a property varying along a flow direction of the fluid. The mixer comprises an inlet configured for receiving an inlet flow, an outlet configured for providing an outlet flow, and a plurality of flow channels coupled between the inlet and the outlet. A flow distributor is provided for distributing the inlet flow into the plurality of flow channels so that each flow channel receives a partial flow from the inlet flow. A flow combiner is provided for combining the partial flows from the plurality of flow channels to the outlet flow. Each flow path comprises a flow direction changer forcing the fluid to flow first in direction changing in respect to the direction of gravitational force. Such mixer provides a mixing characteristic substantially independent of the spatial orientation of the mixer with respect to the orientation of the gravitational force. Accordingly, the mixing behavior of such mixer can be provided to be less vulnerable or even independent of a respective assembly or installation of the mixer in application.

In one embodiment a fluid separation system is provided for separating compounds of a sample fluid in a mobile phase. When a mobile phase including a fluidic sample passes through the fluidic device, for instance driven by high pressure, the interaction between the column packing and the fluidic sample may allow for separating different components of the sample, as performed in a liquid chromatography device.

The fluid separation system comprises a mobile phase drive, such as pumping system, configured to drive the mobile phase through the separation system, and a separation unit, such as a chromatographic column, configured for separating compounds of the sample fluid in the mobile phase. The fluid separation system further comprises a mixer according to any of the aforedescribed embodiments. The mixer can be located anywhere along the flow path of the mobile phase with or without the sample fluid. Preferably, the mixer is provided for mixing the mobile phase before introduction of the sample fluid.

In still another embodiment a flow injection analysis system is provided. In this case a mixer according to any of the afore described embodiments is included into the flow path to provide mixing of the sample components with reagents or with the flow provided through the flow injection analysis system Embodiments of the fluid separation system may comprise a sample injector configured to introduce the sample fluid into the mobile phase, a detector configured to detect separated compounds of the sample fluid, a collection unit configured to collect separated compounds of the sample fluid, a data processing unit configured to process data received from the fluid separation system, and/or a degassing apparatus configured for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

The sample fluid might comprise any type of process liquid, natural sample like juice, body fluids like plasma or it may be the result of a reaction like from a fermentation broth. It may also comprise (but not limited to) sea water, mineral oil or any rectification or cracking fractions of it, extracts of soil, plants or artificial materials such as plastics, as well as alcoholic or alcohol-free beverages.

The pressure in the mobile phase might range from 2-200 MPa (20 to 2000 bar), in particular 10-150 MPa (100 to 1500 bar), and more particular 50-120 MPa (500 to 1200 bar).

Practically, the mixer with a number of flow path channels can be built in a computable design, such as by a "parallel splitter" where an incoming flow is immediately split to a number of channels, each having a desired volume and hydraulic resistance determining the portion of the flow passing through the channel; the distribution profile in the outlet flow is entirely defined by the predesigned dead volumes of the restrictor channels whereby the volume of the inlet chamber is negligible. The above described restrictor channels can be of equal or different hydraulic resistance.

The structure can be planar, the grooves of different width and depth forming the desired system of reservoirs and restrictors. Any part of the appliance can be non-planar, e.g. the restrictor drillings can connect two sides of a plane block, bearing reservoir grooves on each side.

The grooves in a planar structure can be wave-formed or curved to improve radial mixing i.e. mixing of several eluent components flowing side-by-side.

The structure can be of annular design, formed as a system of parallel drillings in a cylinder block, one end of each drilling being connected to the mixer inlet, the other end of each drilling being connected to the mixer outlet. Each drilling consisting of two parts with different diameters, the wider serving as a reservoir, the narrower serving as a restrictor.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION

Figure 1:
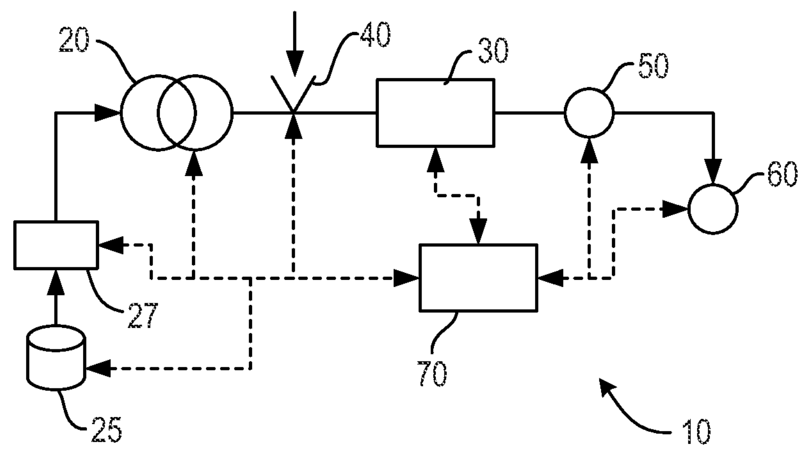
FIG. 1 shows a liquid separation system 10, in accordance with embodiments of the present invention, e.g. used in high performance liquid chromatography (HPLC).

Referring now in greater detail to the drawings, FIG. 1 depicts a general schematic of a liquid separation system 10.

A pump 20 receives a mobile phase from a solvent supply 25, typically via a degasser 27 which reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to introduce or add (often referred to as introduce or inject) a sample fluid into the mobile phase. The stationary phase of the separating device 30 is adapted for separating compounds contained in the sample. A detector 50 can be provided for detecting separated compounds of the sample. A fractionating unit 60 can be provided for collection of separated compounds of the sample.

While the mobile phase can be comprised of one solvent only, it may also be mixed from plurality of solvents. Such mixing might be a low pressure mixing and provided upstream of the pump 20, so that the pump 20 already receives and pumps the mixed solvents as the mobile phase. Alternatively, the pump 20 might comprise plural individual pumping units, each of those receiving and delivering a different solvent or mixture, so that the mixing of the mobile phase (as delivered to the separating device 30) occurs at high pressure side and thus downstream of the pump 20 (or within thereof). The composition of the mobile phase may be kept constant over time, the so called isocratic mode, or varied over time in a controlled manner, the so called gradient mode.

A control and data processing unit 70, which can be a conventional PC, workstation or a dedicated controller, might be coupled (as indicated by the dotted arrows) to one or more of the devices in the liquid separation system 10 in order to receive information and/or to control the operation. For example, the control and data processing unit 70 might control operation of the pump 20 (e.g. setting control parameters) and receive therefrom information regarding the actual working conditions (such as output pressure, flow rate, etc. as measured within the separation system 10 or at certain locations in the flow path, e.g. within the pump unit 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as pressure overtime, flow rate, vacuum level, etc.). The data processing unit 70 might further control operation of the sampling unit 40 (e.g. controlling sample injection). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50).

Figure 2:
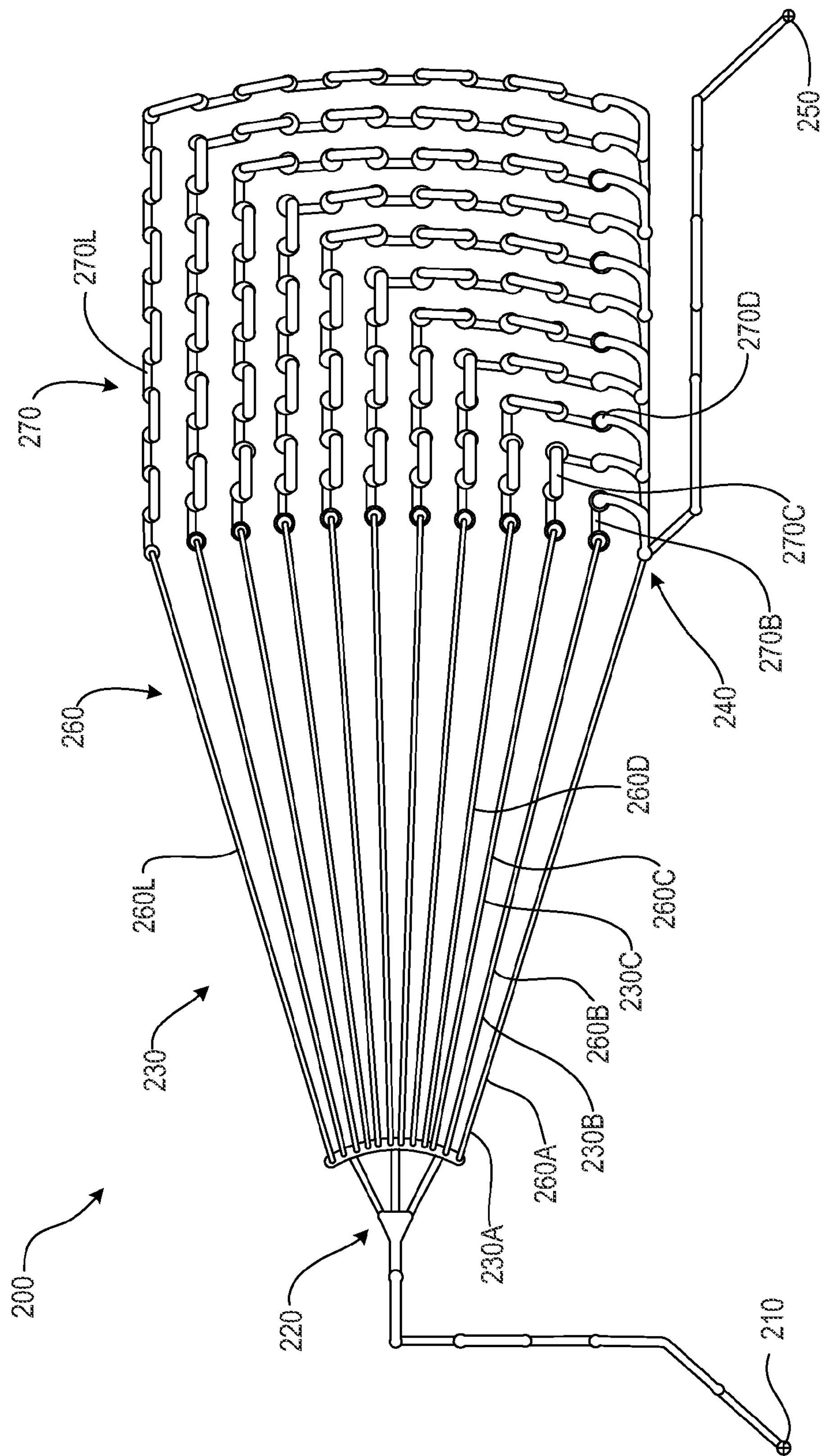
FIG. 2 shows an embodiment of a mixer 200 according to the present invention.

FIG. 2 shows an embodiment of a mixer 200 according to the present invention. The mixer 200 is used for mixing a fluid property such as composition, viscosity, elution strength or temperature, which might vary along a flow direction of the fluid. While the mixer 200 can be situated substantially anywhere in a fluid flow path where varying fluid properties are expected, a preferred application is in the liquid separation system 10 as schematically depicted in FIG. 1. In such liquid separation system 10, the mixer 200 is preferably located in the flow path between the pump 20 and the separating device 30, and more preferably before the sampling unit 40. The mixer 200 may also be part (e.g. integral, releaseably or non-releaseably attached) of one or more components, such as the pump 20, the separating device 30, and the sampling unit 40.

In the embodiment of FIG. 2, the mixer 200 comprises an inlet 210 receiving an inlet flow of the fluid to be mixed. A flow distributor 220 receives the flow from the inlet 210 and distributes it—in parallel—into a plurality of flow channels 230. Accordingly, the flow distributor 220 provides a plurality of parallel partial flows into the plurality of (parallel) flow channels 230.

The flow distributor 220 of FIG. 2 is designed so that it substantially simultaneously distributes the fluid into the first sections 230 and/or that a variation of the property of the fluid arrives substantially simultaneously at the first sections 260.

In the embodiment of FIG. 2, the flow distributor 220 comprises a multi-stage configuration that provides simultaneous arrival of a given partial fluid volume to all the restrictor channels in combination with low distributor volume. Other embodiments are also possible in order to achieve lowest total volume of the distributor.

The plurality of flow channels 230 eventually couple to a flow combiner 240, which combines the partial flows from the plurality of flow channels 230 and provides them to an outlet flow. The outlet flow is output by an outlet 250. The flow combiner 240 is preferably designed to provide a minimum volume, as such volume of the flow combiner 240 typically contributes mainly to delay and less to mixing properties.

Each of the plurality of flow channels 230 comprises a first flow section 260, and some of the flow channels 230 further comprise a second flow section 270 coupled in series to the respective first flow section 260. In the embodiment of FIG. 2, a first flow channel 230A comprises (only) a first flow section 260A coupling directly between the flow distributor 220 and the flow combiner 240. A second flow channel 230B comprises a first flow section 260B coupling to a second flow section 270B, which then also couples into the flow combiner 240. Accordingly, a third flow channel 230C comprises a first flow section 260C coupling into a second flow section 270C, which then couples to the flow combiner 240. This continues accordingly for further flow channels. In FIG. 2, further first flow sections 260D-260L and second flow sections 270D-270L are shown, each coupling in series and eventually to the flow combiner 240.

The first flow sections 260A-260L are designed to provide a significantly larger hydraulic resistance than the respective second flow section 270B-270L, so that the total hydraulic resistance of each flow channel 230 is dominated by the hydraulic resistance of the respective first flow section 260. Further in the specific embodiment of to FIG. 2, all of the first flow sections 260A-260L are designed to have substantially the same length and cross section, so that each first flow section 260 substantially has the same hydraulic resistance. Considering that the hydraulic resistance of each flow channel 230 is dominated by its respective first flow section 260, it can be assumed that each flow channel 230 can be regarded as providing substantially the same hydraulic resistance to the fluid when introduced into the flow channels 230 at the flow distributor 220. When designing the flow distributor 220 to distribute the inlet flow substantially evenly into the flow channels 230, it can be assumed that the partial flow in each flow channel is substantially equal. The distribution of the partial flows into the flow channels 230 in such embodiment is substantially independent of the viscosity of the fluid.

While the hydraulic resistance of each flow channel 230 is dominated by its respective first flow section 260, each second flow section 270 has a volume delaying fluid propagation (from the respective first section 260 to the flow combiner 240) by a time required by the respective partial flow to pass the volume of the respective second flow section 270. In each flow channel 230, the volume of the second flow section 270 is designed to be significantly larger than a volume of the respective first flow section 260. In such embodiment, the propagation of each partial flow will be mainly influenced by the volume of the respective second flow section. By providing different volumes of the respective second flow sections 270, a (desired) flow characteristic can be obtained. By having at least one flow channel 230 without second flow section, the total resulting flow characteristic of the mixer 200 can be designed to have the minimum delay as resulting from the first flow section 260 only.

Figure 3A:
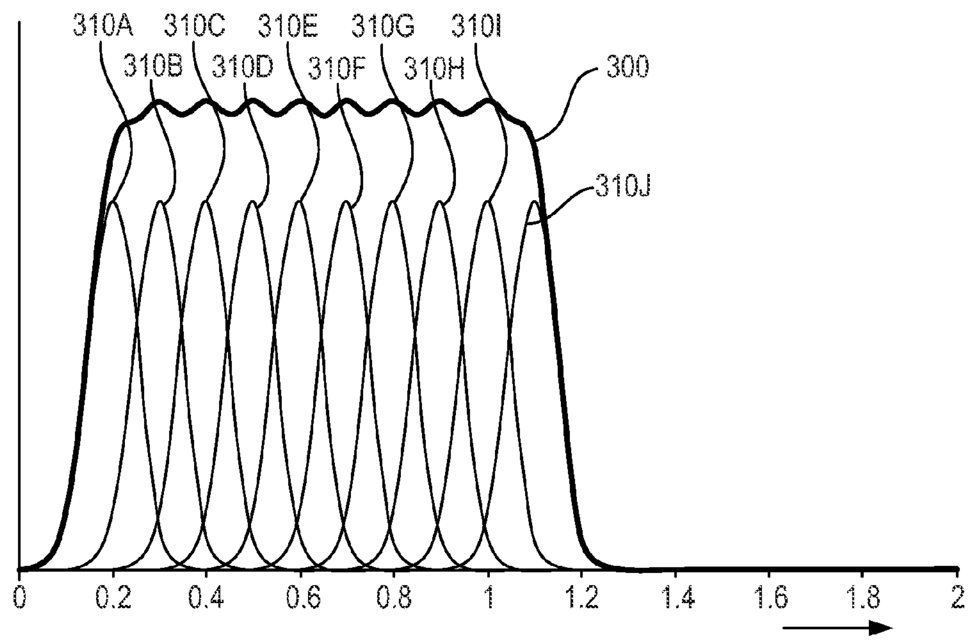
FIGS. 3A and 3B illustrate examples of mixing functions resulting from an embodiment in according with FIG. 2.

FIG. 3A illustrates in an example a mixing function 300 depicting the theoretical distribution of a very narrow (in terms of volume) property variation in the fluid flow after the latter has passed through the mixer over time or over the passed volume. The mixing function 300 may result from an embodiment in accordance with FIG. 2, however with the difference that such mixer 200 providing the mixing function of FIG. 3A shall have only ten flow channels 260 in contrast to the twelve flow channels in the embodiments shown in FIG. 2. Each partial flow through the flow channels 260 results in a partial flow profile 310A-310J, which are then superimposed to the mixing function 300. Partial flow profile 310A shall result from a flow channel with only a first flow section such as the first flow section 260A in FIG. 2, thus exhibiting the minimum delay time of all partial flow profile 310A-310J. Partial flow profile 310B shall result from a flow channel with first and second flow sections such as the first flow section 260B and the second flow section 270B in FIG. 2. Correspondingly, flow profile 310C shall result from a flow channel with first and second flow sections, such as the first flow section 260C and the second flow section 270C. The second flow section 270C (corresponding to the flow profile 310C) is designed to have a larger volume than the second flow section 270B, so that the flow profile 310C is further delayed (with respect to the flow profile 310A) than the flow profile 310B. By designing each of the second flow sections 270 to have a different volume, the flow functions 310B-310J each provide a different delay with respect to the flow profile 310A resulting from the propagation through the first flow section 260A only. By adequately designing the respective volumes of the second flow section 270, many different desired profile of the mixing function 30 can be achieved. It is also clear that multiples of the second flow sections 270 may have a same volume, so that a different that the substantially "flat" shape of the mixing function 300 can be achieved.

Figure 3B:
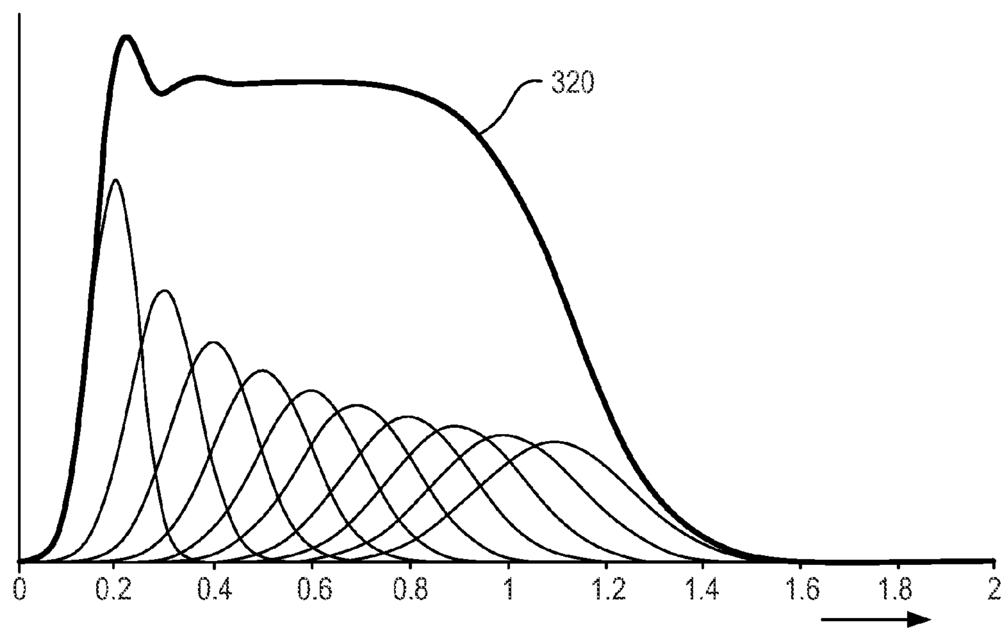

FIG. 3B shows a mixing function 320 also resulting from a plurality of partial flows with different delays. In contrast to the example of FIG. 3A, the mixing function 320 of FIG. 3B shows an effect of increasing dispersion for different channels, which represents the effect of the dispersion of the property variation within a single partial flow as it passes through its corresponding partial channel. The extent of this additional distribution is determined by the partial channel design (especially by the design of the second section).

Figure 4:
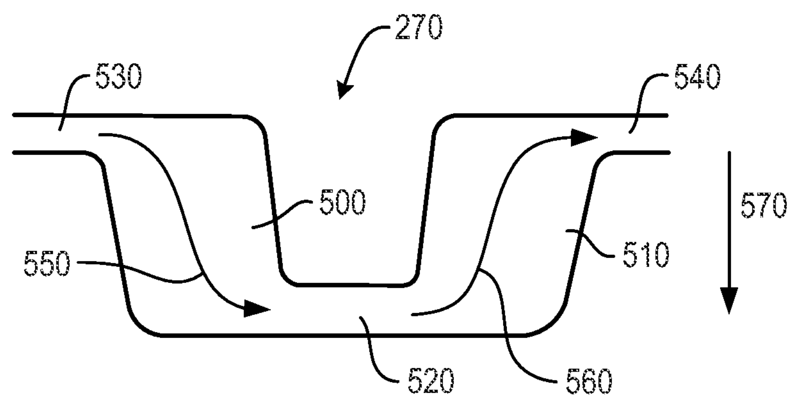
FIG. 4 shows in cross sectional view an embodiment of a part of a second flow section.

FIG. 4 shows in cross sectional view an embodiment of the second flow section, or at least a part thereof, as may be applied in the embodiments of FIG. 2. It is noted that the partially three dimensional illustration of FIG. 2, the second flow channels 270 are depicted indicating a three-dimensional structure corresponding to FIG. 4.

In FIG. 4, the second flow channel 270 comprises a first chamber 500 and a second chamber 510 sequentially arranged in flow direction of the fluid and coupled by a connection section 520. The chambers 500 and 510 provide a cross section in flow direction which is significantly larger than the cross section of the connecting section 520. In the depiction of FIG. 4, the cross section in flow direction is perpendicular to the plane of the drawing. The volume of each of the first and second chambers 500 and 510 is designed to be significantly larger than a volume of the connecting section 520, so that a resulting flow delay is mainly dominated by the volume of the chambers 500 and 510.

In the embodiment of FIG. 4, the flow entry (e.g. from the respective first flow section) shall be at the top left side as denoted with reference numeral 530, and fluid exit shall be at the top right side as denoted with reference numeral 540 (e.g. to the flow combiner 240). As apparent from FIG. 4, flow entry 530 is located in the first chamber 500 at the opposite side and height than the connecting section 520. Accordingly, the fluid flow through the first chamber 500 is depicted by arrow 550. With the connecting section 520 opening into the second chamber 510 at opposing side and height than the flow exit 540, the flow through the second chamber 510 will follow substantially as shown by arrow 560. Arrow 570 shall represent the direction of gravitational force.

In the embodiment of FIG. 4, the flow direction 550 in the first chamber 500 has a component into the direction of the gravitational force 570, while the flow direction 560 shows a direction component in opposite direction to the gravitational force 570. This also applies even if the direction of gravitational force is tilted (by less than ninety degree in each direction) with respect to the direction as indicated by arrow 570 in FIG. 4. Accordingly, the second flow section 270 of FIG. 4 provides a direction change element for changing flow of the liquid with respect to the gravitational force 570. Such forcing of the fluid to change direction of flow with respect to gravitational force 570 can reduce or even avoid the effect of fluid component sedimentation, which might occur in larger volumes in case partial segments of not yet completely mixed fluids have different density or specific gravity values and are thus subject to sedimentation or separation in the gravitational field according to their density. In such case, the forces caused by so-called dynamic pressure differences applied to these partial segments should be greater than the (Archimedes) force differences originating from the specific gravity variation. One way to achieve this is to reduce the size of "compact" fluid volumes by splitting a second section to a system of interconnected chambers.

While a single chamber (to provide the second flow section 270) might be sufficient in certain applications, it has been found that plural chambers (as in FIGS. 2 and 4) allow designs having a higher mechanical stability and also avoid that fluid components with different density properties may separate within the chamber and lead to such aforedescribed fluid component segmentation.

The mixer 200 (e.g. in FIG. 2) is preferably designed so that the flow-through times of the partial flows through the first sections 260 are substantially neglectable as compared to a characteristic duration of a variation of the varying property of the fluid. For example, in case of an HPLC system as shown in FIG. 1 with the pump 20 producing liquid packages of different composition, the mixer 200 is preferably designed so that the flow-through time through the first section 260 is smaller and preferably much smaller than a propagation time of the smallest solvent composition package through the first section, and more preferred through the mixer 200. This can be achieved by adapting the respective cross sections lengths and volumes accordingly.

The restrictor channels of the first sections 260 may have dimensions of about 0.1×0.12×20 mm. The second sections 270 (e.g. 0 to 24 chambers) may have dimension of 1 mm high and 0.8 mm or smaller inner diameter.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A mixer for mixing a fluid having a property varying along a flow direction of the fluid, the mixer comprising:

an inlet configured for receiving an inlet flow, an outlet configured for providing an outlet flow, and a plurality of flow channels coupled between the inlet and the outlet, a flow distributor for distributing the inlet flow into the plurality of flow channels so that each flow channel receives a partial flow from the inlet flow, and a flow combiner for combining the partial flows from the plurality of flow channels to the outlet flow, wherein each flow channel comprises a first flow section having a hydraulic resistance substantially representing a hydraulic resistance of the flow channel, one or more of the flow channels each comprise a second flow section coupled in series with the first flow section of the respective flow channel, each second flow section comprises a volume that is flown through by the fluid and delays fluid propagation from the first flow section to the flow combiner by a time required by the respective partial flow to pass the volume of the respective second flow section, and the distribution of the partial flows into the flow channels is substantially independent of the viscosity of the fluid.

2. The mixer of claim 1, comprising at least one of:

the hydraulic resistance of each of the plurality of flow channels is substantially equal;

the volume of the second flow section is significantly larger than a volume of the first flow section of the respective flow channel;

the distribution of the partial flows into the flow channels is substantially independent of the viscosity of the fluid at any moment in time.

3. The mixer of claim 1, comprising at least one of:

the flow distributor distributes the fluid into the first flow sections of the plurality of flow channels;

the flow distributor substantially simultaneously distributes the fluid into the first flow sections;

a variation of the property of the fluid arrives substantially simultaneously at the first flow sections.

4. The mixer of claim 1, comprising at least one of:

the flow-through times of the partial flows through the first flow sections are substantially equal;

the flow-through times of the partial flows through the first flow sections are substantially neglectable to a characteristic duration of a variation of the varying property of the fluid;

the flow-through times of the partial flows through the first flow sections are substantially equal and neglectable to a characteristic duration of a variation of the varying property of the fluid;

the flow-through time of each partial flow through the respective first flow section is smaller than a characteristic duration of a variation of the varying property of the fluid.

5. The mixer of claim 1, comprising at least one of:

a plurality of the second flow sections each has a different volume for delaying the partial flow of the respective flow channel by a different time period;

the volume of each of a plurality of the second flow sections is configured so that the output flow has a desired flow delay profile with respect to the input flow;

the volume of each second flow section is significantly larger than a volume of the first flow section of the respective flow channel.

6. The mixer of claim 1, comprising at least one of:

one or more of the second flow sections each comprises a chamber;

one or more of the second flow sections each comprises a plurality of chambers arranged sequentially in the flow direction of the fluid and having a total volume being significantly larger than a volume of the first flow section of the respective flow channel.

7. The mixer of claim 1, wherein:

one or more of the second flow sections each comprises a plurality of chambers arranged sequentially in the flow direction of the fluid, wherein successive chambers are coupled by a respective connecting section.

8. The mixer of claim 7, comprising at least one of:

each chamber has an average cross section being significantly larger than an average cross section of a respective connecting section coupled to such chamber;

each chamber has a chamber volume being significantly larger than a volume of a respective connecting section coupled to such chamber;

wherein a plurality of the connecting sections are arranged with respect to the respective chambers to force the fluid to flow at varying angles with respect to direction of gravitational force.

9. The mixer of claim 1, wherein one or more of the second flow sections each comprises at least one direction change element configured for changing the flow direction of the fluid.

10. The mixer of claim 9, wherein the direction change element comprises at least one first subsection having a first direction of flow of the fluid, and at least one second subsection having a second direction of flow of the fluid, the first direction of flow being inclined with respect to the second direction of flow.

11. The mixer of claim 10, comprising at least one of:

the first direction of flow is vertical and the second direction of flow is horizontal;

at least one of the first and second directions of flow has a direction component in the direction of gravitational force.

12. The mixer of claim 1, comprising at least one of:

each flow channel comprises a respective first flow section and a respective second flow section coupled in series, the hydraulic resistance of the first flow section being significantly larger than a hydraulic resistance of the second flow section thus dominating the hydraulic resistance of the flow channel;

the hydraulic resistance of the first flow section is in the range of 2-100000 times, preferably 5-500 times, and more preferably about −100 times, larger than the hydraulic resistance of the second flow section;

in each flow channel, a first cross section of the first flow section is significantly smaller than a second cross section of the second flow section thus dominating the hydraulic resistance of the flow channel.

13. The mixer of claim 1, comprising at least one of:

each first flow section is substantially equal in length in flow direction of the fluid;

the fluid is at least one of a liquid and a gas;

the varying property of the fluid is at least one of a physical and chemical property varying along the flow direction of the fluid;

the varying property of the fluid is at least one of temperature, composition, viscosity, and elution strength varying along the flow direction of the fluid.

14. A fluid separation system for separating compounds of a sample fluid in a mobile phase, the fluid separation system comprising:

a mobile phase drive configured to drive the mobile phase through the fluid separation system, a separation unit configured for separating compounds of the sample fluid in the mobile phase, a mixer according to claim 1.

15. The fluid separation system of claim 14, further comprising at least one of:

the mixer is arranged in a flow path between the mobile phase drive and the separation unit;

a sample injector configured to introduce the sample fluid into the mobile phase;

a detector configured to detect separated compounds of the sample fluid;

a collection unit configured to collect separated compounds of the sample fluid;

a data processing unit configured to process data received from the fluid separation system;

a degassing apparatus configured for degassing the mobile phase.

* * * * *